United States Patent
Roitt et al.

(10) Patent No.: US 6,469,139 B1
(45) Date of Patent: Oct. 22, 2002

(54) MODIFIED HUMAN CHORIONIC GONADOTROPIN (β-HCG) PROTEINS AND THEIR MEDICAL USE

(75) Inventors: Ivan Maurice Roitt; Peter John Delves; Torben Lund, all of London (GB)

(73) Assignee: University College London, London (GB)

(*) Notice: Subject to any disclaimer, the term of this patent is extended or adjusted under 35 U.S.C. 154(b) by 0 days.

(21) Appl. No.: 08/983,397

(22) PCT Filed: Jul. 19, 1996

(86) PCT No.: PCT/GB96/01717

§ 371 (c)(1),
(2), (4) Date: May 13, 1998

(87) PCT Pub. No.: WO97/04098

PCT Pub. Date: Feb. 6, 1997

(30) Foreign Application Priority Data

Jul. 19, 1995 (GB) .............................................. 9514816

(51) Int. Cl.[7] .......................... C07K 1/00; C07K 14/00; C07K 17/00; C12P 21/06

(52) U.S. Cl. ...................... 530/350; 530/827; 530/850; 530/402; 530/403; 435/69.1; 435/252.3; 435/471

(58) Field of Search ............................... 435/69.1, 70.1, 435/71.1, 71.2, 252.3, 32.1, 325, 471; 530/350, 402, 403, 827, 850; 536/23.5

(56) References Cited

U.S. PATENT DOCUMENTS

| | | |
|---|---|---|
| 4,302,386 A | 11/1981 | Stevens |
| 4,310,455 A | 1/1982 | Bahl |
| 4,803,164 A * | 2/1989 | Hitzeman et al. |
| 4,966,888 A | 10/1990 | Saxena et al. |

FOREIGN PATENT DOCUMENTS

| | | |
|---|---|---|
| FR | 2 319 379 | 2/1977 |
| WO | WO 91/16922 | 11/1991 |
| WO | WO 94/07530 | 4/1994 |
| WO | WO 95/20600 | 8/1995 |
| WO | WO 97/04098 | 2/1997 |

OTHER PUBLICATIONS

R.D. Ghai et al., "Immunological Properties of the β–Subunit of Human Chorionic Gonadotropin. I. Effect of Chemical and Enzymatic Modifications," *Endocrinology*, 107:1556–1563 (1980).
O.P. Bahl et al., "Immunological Properties of the β–Subunit of Human Chorionic Gonadotropin," *Biochemical and Biophysical Research Communications*, 70(2):525–532 (1976).
S. Dirnhofer et al., "Functional and immunological relevance of the COOH–terminal extension of human chorionic gonadotropin β: implications for the WHO birth control vaccine," *The FASEB Journal*, 7:1381–1385 (1993).
W.R. Moyle et al., "Localization of Residues That Confer Antibody Binding Specificity Using Human Chorionic Gonadotropin/Luteinizing Hormone β Subunit Chimeras and Mutants," *The Journal of Biological Chemistry*, 265(15):8511–8518 (May 25, 1990).
S. Dirnhofer et al., "The molecular basis for epitopes on the free β–subunit of human chorionic gonadotrophin (hCG), its carboxyl–terminal peptide and the hCGβ–core fragment," *Journal of Endocrinology*, 141:153–162 (1994).
A.M. Jackson et al., "Identification and selective destruction of shared epitopes in human chorionic gonadotropin beta subunit," *Journal of Reproductive Immunology*, 31:21–36 (1996).
A.M. Jackson, et al., "Construction of hCG Epitope–Loss Mutants," The 9th International Congress of Immunology, Abstract Book, No. 1131, p. 191 (Jul. 23–29, 1995) (Abstract Only).
R.M. Horton et al., "Recombination and mutagenesis of DNA sequences using PCR," from *Directed Mutagenesis: A Practical Approach*, Ed. McPherson MJ, IRL Press, pp. 217–247 (1991).
P. Berger et al., "Monoclonal antibodies against the free subunits of human chorionic gonadotrophin," *Journal of Endocrinology*, 125:301–309 (1990).
W.R. Jones et al., Phase I Clinical Trial of a World Health Organisation Birth Control Vaccine, *The Lancet*, pp. 1295–1298 (Jun. 11, 1988).
V.C. Stevens et al., "Antifertility Effects of Immunization of Female Baboons With C–Terminal Peptides of the β–Subunit of Human Chorionic Gonadotropin," *Fertility and Sterility*, 36(1):98–105 (1981).
I.M. Roitt, "Basic concepts and new aspects of vaccine development," *Parasitology*, 98:S7–S12 (1989).
B. Seed, "An LFA–3 cDNA encodes a phospholipid–linked membrane protein homologous to its receptor CD2," *Nature*, 329:840–842 (1987).
K. Talmadge et al., "Evolution of the genes for the β Subunits of human chorionic gonadotropin and luteinizing hormone," *Nature*, 307:37–40 (1984).
J.P. Hearn, "Immunization against pregnancy," *Proc. R. Soc. Lond. B.*, 195:149–160 (1976).
G.P. Talwar et al., "A vaccine that prevents pregnancy in women," *Proc. Natl. Acad. Sci. USA*, 91:8532–8536 (Aug. 1994).
L.M. Roitz, "Antigens can be synthesized through gene cloning," *Essential Immunology*, Blackwell Scientific Publications, p. 281 (1994).
B. Seed et al., "Molecular cloning of the CD2 antigen, the T–cell erythrocyte receptor, by a rapid immunoselection procedure," *Proc. Natl. Acad. Sci. USA*, 84:3365–3369 (May 1987).

* cited by examiner

Primary Examiner—Gary L. Kunz
Assistant Examiner—Robert S. Landsman
(74) Attorney, Agent, or Firm—Akin, Gump, Strauss, Hauer & Feld, L.L.P.

(57) ABSTRACT

The present invention relates to modified human chorionic gonadotropin (β-hCG) proteins and their medical use as immunological contragestatives. The modification causes a reduction in the cross-reactivity of the modified β-hCG protein with luteinizing hormone (LH) as defined by the ability of both proteins to react with the same antibody.

33 Claims, 5 Drawing Sheets

Figure 1:
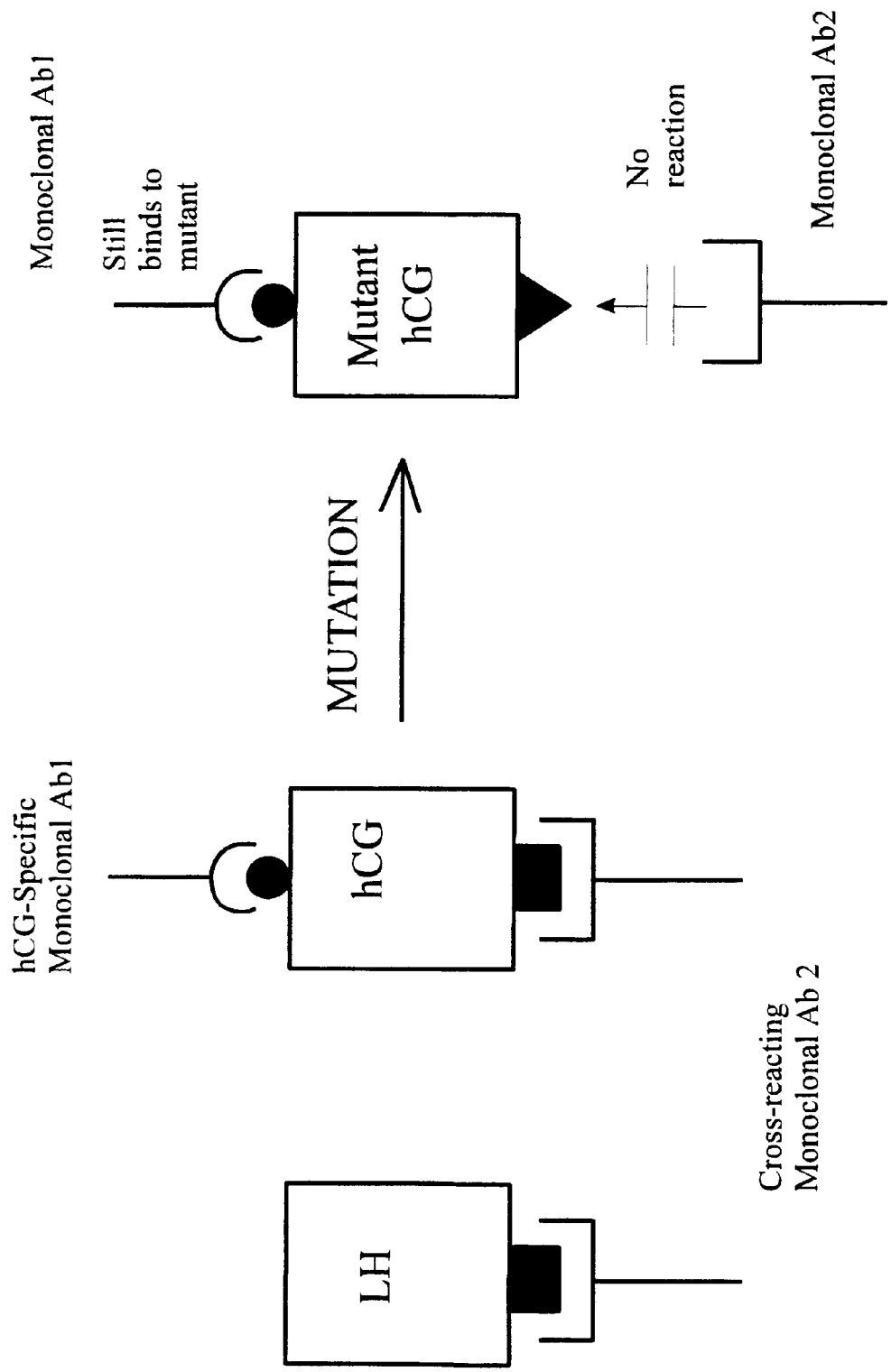
Figure 2A:
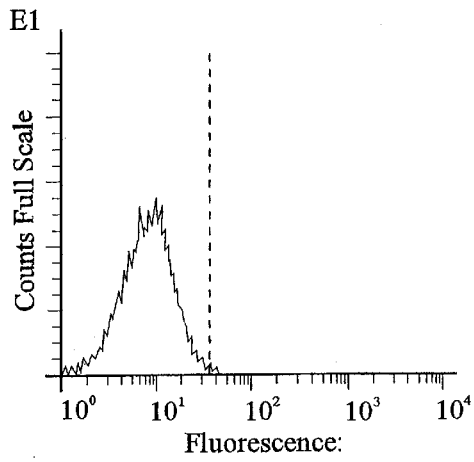
Figure 2B:
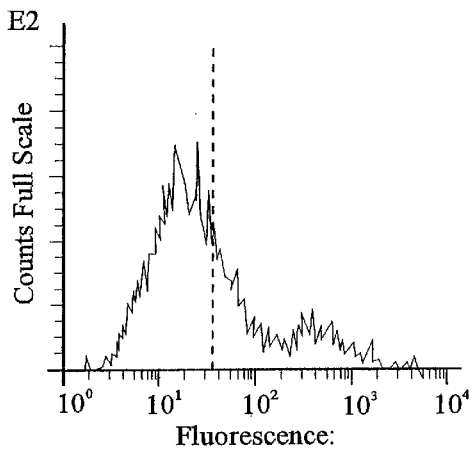
Figure 2C:
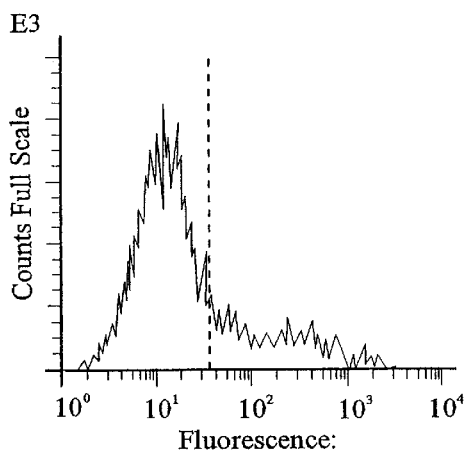
Figure 2D:
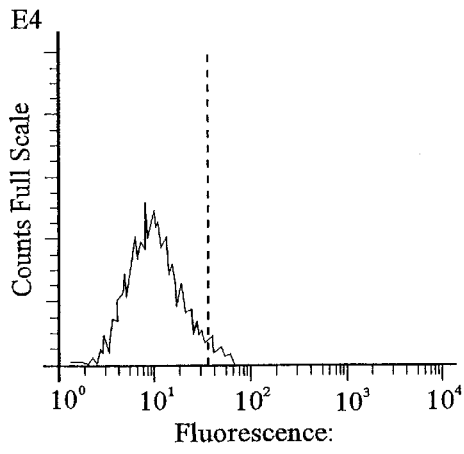
Figure 3:
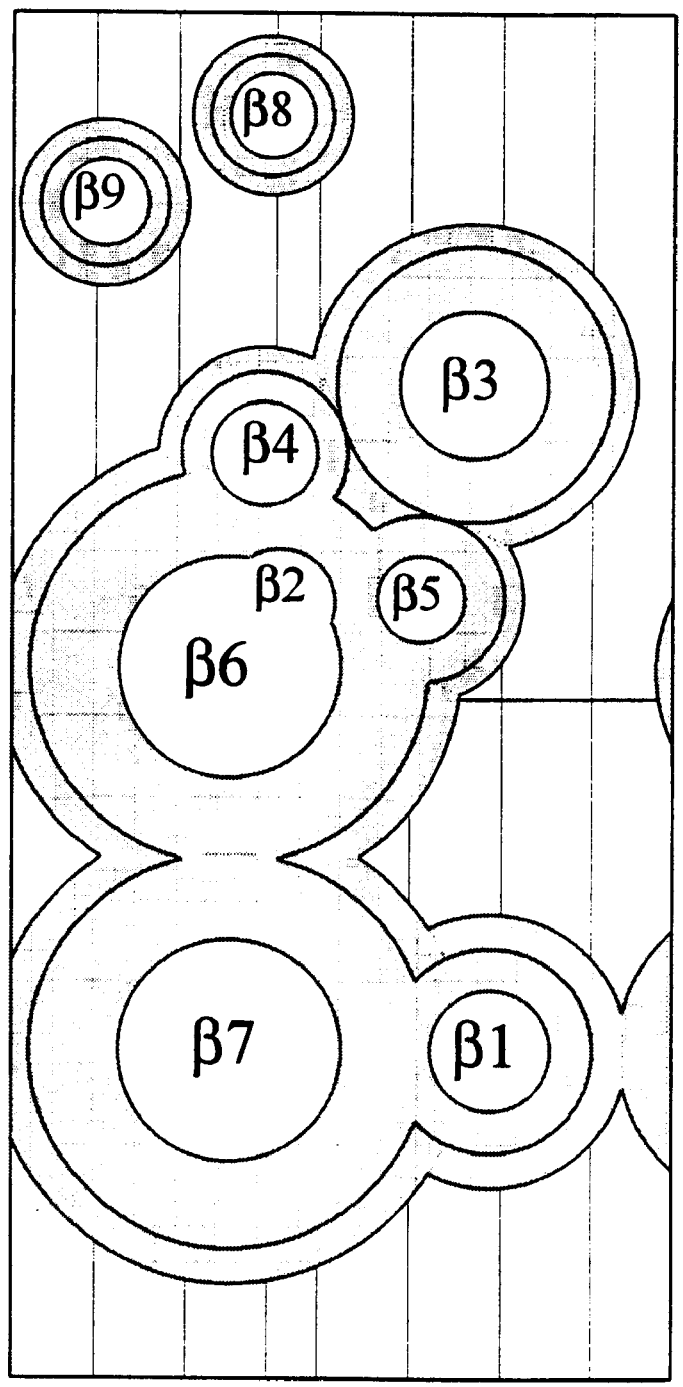

| mAb | Epitope cluster | | WT | 1 | 2 | 3 | 4 | 5 | 6 | 7 | 8 | 9 | 10 | 20 |
|---|---|---|---|---|---|---|---|---|---|---|---|---|---|---|
| INN-hCG-2 | ß1 | CG | | | | | | | | | | | | |
| INN-hCG-32 | ß1 | CG | | | | | | | | | | | | |
| INN-hCG-22 | ß2 | CG/LH | | | | N | | | | N | | | | |
| INN-bLH-1 | ß3 | CG/LH | | | N | N | N | N | | N | N | | | |
| INN-hCG-111 | ß3 | CG/LH | | | N | N | N | | N | N | N | | | |
| INN-hCG-24 | ß4 | CG/LH | | | | N | | | | N | | | | |
| INN-hCG-58 | ß5 | CG/LH | | | | N | | | | N | | | | |
| INN-hCG-51 | ß3/5 | CG/LH | | | | N | | | | N | | | | |
| INN-hCG-20 | ß3/5 | CG/LH | | | | N | | | | N | | | | |
| 3E2 | ß3/5 | CG/LH | | | | N | | | | N | N | | | N |
| INN-hCG-64 | ß6 | CGß | | N | | N | N | | | | | N | | |
| INN-hCG-68 | ß7 | CGß | | | | | | | | | | | | |
| OT3A | C term. | | | | | | | | | | | | | |

Table 1 : Binding of mAbs to wildtype (WT) and mutant hCGß molecules expressed on COS7 cells. All MAbs recognise conformationally-dependent epitopes except OT3A which is against a linear epitope (a.a. 133-139) on the C terminus.

mAb binding equivalent to that of OT3A (cells positive >70% relative to OT3A).

mAb binding reduced compared to that of OT3A (cells positive 50-70% relative to OT3A).

mAb binding reduced compared to that of OT3A (cells positive 20-30% relative to OT3A).

N
mAb abolished (<10% relative to OT3A)

Figure 4

C-terminal loop changes

| Mutant | amino acids changed |
|---|---|
| 3 | 68 Arg → Glu |
|   | 74 Arg → Ser |
|   | 75 Gly → His |
|   | 79 Val → His |
| 7 | 68 Arg → Glu |
| 8 | 74 Arg → Ser |
|   | 71 Gly → Arg |
| 9 | 75 Gly → His |
| 10 | 79 Val → His |
| 20 | 74 Arg → Ser |

N-terminal loop changes

| Mutant | amino acids changed |
|---|---|
| 1 | 20 Lys → Asn |
|   | 21 Glu → Arg |
|   | 22 Gly → Glu |
| 2 | 24 Pro → His |
|   | 25 Val → Tyr |
| 4 | 20 Lys → Asn |
|   | 21 Glu → Arg |
|   | 22 Gly → Glu |
|   | 24 Pro → His |
|   | 25 Val → Tyr |
| 5 | 24 Pro → His |
| 6 | 25 Val → Tyr |

Figure 5 (Table 2)

MODIFIED HUMAN CHORIONIC GONADOTROPIN (β-HCG) PROTEINS AND THEIR MEDICAL USE

CROSS-REFERENCE TO RELATED APPLICATION

This application is a 35 USC § 371 filing of International Application No. PCT/GB96/01717, filed Jul. 19, 1996.

FIELD OF THE INVENTION

The present invention relates to substances, in particular to modified human chorionic gonadotropin (β-hCG) proteins/genes, and their medical use, for example as immunological contraceptives having improved specificity and/or which in vivo avoid producing antibodies having undesirable cross-reactivity, for example with other natural hormones.

BACKGROUND OF THE INVENTION

The principle of immunising the female with β-hCG or its C-terminal peptide to induce antibodies which neutralise hCG and therefore inhibit pregnancy has been proposed[1] and has been the subject of trials by the World Health Organization[2] and the Indian Health Authorities[3].

Shortly after fertilization of the ovum, the hormone hCG which at other times is essentially absent from the body, is produced and acts on the corpus luteum in the ovary to promote synthesis of progesterone. Progesterone is vital for the maintenance of the fertilized egg in the uterus and so the production of antibodies to neutralise the hCG will effectively prevent the pregnancy from proceeding. This strategy has been successfully employed to block fertility in baboons[1] and marmosets[4] and more recently in humans[3].

hCG itself is composed of two chains, α and β. The α-chain is common to other hormones (FSH, TSH and LH), which contribute to normal physiological function, so that autoantibodies made to this chain would be highly undesirable. The β-chain of hCG is far more specific, but a major problem still remains in that there is an 85% homology of β-hCG with the β-chain of luteinizing hormone (LH) which is present continually in the potentially fertile female. A strategy adopted by the W.H.O. has been to prepare a vaccine based on the β-hCG C-terminal peptide (residues 109–145) which is unique to hCG. This is made immunogenic by linking to the carrier proteins tetanus or diphtheria toxoids to provide T-cell help. This has not produced adequately high responses in high frequency within the cohorts tested[5] partly because of the relatively weak immunogenicity of the peptide and the fact that antibodies to a peptide fragment of a protein do not usually bind with high affinity to the parent protein[6].

Talwar adopted a less cautious approach by using the whole β-hCG chain (together with ovine α-chain as a carrier) in the hope that the antibodies produced which cross-reacted with LH would not prove to be troublesome. However, not enough experience has been gained so far to confirm this hope and in principle, where possibly millions of people could be immunized with the vaccine for several years, it would seem prudent, to devise a vaccine which did not cross-react with LH.

SUMMARY OF THE INVENTION

It is known that the epitopes specific for β-hCG other than the C-terminus are discontinuous, i.e. the residues making up the epitope may be separate from each other in primary structure but are brought together by the protein folding. However, the contact residues forming these discontinuous epitopes are very difficult to identify and even if they could be, the "floppiness" of any synthetic peptide formed from these residues would make it a poor immunogen with respect to the generation of antibodies with high affinity.

In the present invention, we have adopted a strategy[7] which relies upon the natural folding of the protein to form the specific discontinuous epitope, while at the same time mutating the parent gene in such a way that the amino acid residues forming the LH cross-reacting epitopes are altered without affecting the more distant folding of the hCG-specific epitope(s). The retention of the desired epitope(s) and the loss of the unwanted epitopes can be monitored by reaction of the mutants with monoclonal antibodies specific for hCG and others giving cross-reaction between hCG and LH.

Broadly, the present invention provides a substance which has the property of inducing a neutralising antibody response to β-hCG in vivo, said antibodies not substantially cross-reacting with LH, the substance comprising one or more of the conformational epitopes specific to native β-hCG, or functional equivalents or mimetics of these epitopes.

In one aspect, the substance is a modified β-hCG protein having one or more conformational epitopes specific to native β-hCG, the protein being modified at one or more amino acid residues forming epitope(s) of native β-hCG that cross-react with LH, to reduce the cross-reactivity the β-hCG protein with LH, as defined by the ability of both proteins to react with the same antibody. The present invention also includes substances which are variants, derivatives, functional equivalents or mimetics of these above proteins.

Preferably, the substance includes two or more epitopes that are specific to native β-hCG. This helps to induce the production of antibodies specific for these epitopes, which will form complexes of the β-hCG with two or more antibody molecules, so helping to improve the in vivo neutralising activity caused by the substance.

Preferably, the modified amino acid residues are selected from the following residues of native β-hCG; Lys20, Glu21, Gly22, Pro24, Val25, Glu65, Arg68, Gly71, Arg74, Gly75 and/or Val79.

There are other residues common to β-hCG and β-LH which lie on the outside of the protein molecule accessible to the aqueous solvent phase, which might potentially be immunogenic and give rise to cross-reacting antibodies. This would have to be established following immunisation with the mutant β-hCG and a similar further mutation procedure would then be required to abolish the epitopes reacting with these new antibodies.

The rationale for selecting the residues to replace the native residues is set out below in more detail. Preferred modifications are set out in table 2.

In a further aspect, the present invention provides nucleic acid encoding the above proteins, vectors incorporating the nucleic acid and host cells transformed with the vectors.

In a further aspect, the present invention includes compositions comprising one or more of the above substances, in combination with a physiologically acceptable carrier. Preferably, the compositions will be contraceptive compositions in a form suitable for immunisation. However, the substances, proteins or compositions described herein may prove useful in hCG-specific immunoassays and for applications where hCG is active, such as the inhibition of Kaposi sarcoma.

In a further aspect, the present invention provides a method of contraception, more strictly in this context contragestative, for a female mammal comprising immunising the female mammal with a contraceptively effective amount of one or more of the substances.

In a further aspect, the present invention includes the use of the substances in the manufacture of a contraceptive composition.

Conveniently, the immunogenicity of the substance may be enhanced by linking it to a carrier such as tetanus toxoid, or to appropriate sequences from such a carrier acting as T-helper epitopes. Additionally the substance may be engineered as a fusion protein with an appropriately immunogenic partner. Engineered DNA constructs containing nucleotide sequences encoding the substance together with, for example, additional sequences encoding T-helper epitopes or cytokine adjuvants, may be directly administered as a nucleic acid, preferably DNA, vaccine.

It will be appreciated that the nucleic acid construct encoding the modified β-hCG protein can be used as an initial vaccine to prime an immune response. This initial response can then be boosted by subsequent injection of the modified β-hCG protein itself. Likewise, the modified β-hCG protein could be used first followed by the nucleic acid to boost the immune response.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled according to its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The present invention will now be described in more detail by way of example with reference to the accompanying drawings.

BRIEF DESCRIPTION OF THE DRAWINGS

FIG. 1 shows schematically a modified β-hCG protein in which an epitope which cross-reacts with LH is modified; more particularly an epitope deletion mutant which has lost epitope (■) cross-reacting with β-LH but still retains β-hCG specific epitope (●).

FIG. 2 comprises FIGS. 2A–2D, and shows the fluorescence of cell transfected with β-hCG mutant 6 determined by Facscan: 2A-control antibody; 2B-stained by anti-C terminal epitope; 2C-stained by anti-hCG-specific $β_1$ epitope; 2D-stained with antibody to LH cross-reacting $β_3$ epitope showing loss of staining;

FIG. 3 shows the relative spatial distribution of the β-hCG epitope clusters;

FIG. 4 shows the results of the binding of Mabs to different mutants; and,

FIG. 5 shows the amino acid substitutions made in β-hCG.

DETAILED DESCRIPTION

Production of Mutant β-hCG

β-hCG has a size of 145 amino acid residues which include 12 cysteines that form 6 conserved di-sulphide bridges. The subunit is heavily glycosylated with N-linked carbohydrates at position Asn13 and Asn30in addition to four O-linked carbohydrates in the C-terminus at Ser121, 127, 132 and 138. To ensure correct folding of the recombinant molecules we opted for expression in mammalian cells. Using a construct where β-hCG is synthesized as a fusion protein with a C-terminal extension that consists of the 17 amino acids proximal to the membrane, the transmembrane and the cytoplasmic portion of the H2-$D^b$ molecule, it was possible to express wild type and mutant hCG on the surface of transfected cells. The expression level was determined with the hCG specific Mab OT3A on a Becton Dickinson Facscan as shown in FIG. 2. The Mab OT3A which recognizes a linear epitope in the C-terminal extension of β-hCG can be used to quantitate the expression level of the wild type and mutant recombinant proteins following transient transfection in the COS7 cells.

Berger et al[8&9] have previously used a panel of Mab to define 8 separate epitope clusters on β-hCG, which can graphically be related to each other using a cylindrical Mercator's projection (FIG. 3). The β1–β5, β8 and β9 clusters are present on the heterodimeric hCG holohormone, whereas β6 and β7 are unique to the free β-hCG subunit. The β1, β6, β7, β8 and β9 are unique to hCG, whereas the Mab to the other epitope clusters cross-react with βLH. All the Mabs used apart from OT3A, recognize discontinuous sequences on β-hCG, because reduction and alkylation of β-hCG abolishes the binding of the Mab[9]. As summarised in Table 1 (FIG. 4) all the Mab against the different β-hCG epitope clusters used in this study bind to surface expressed wild type β-hCG, transiently expressed in COS7 cells. This suggests that the folding of the recombinant wild type β-hCG is as seen in the native molecule.

The target residues for mutation were selected from the crystal structure of hCG to have side chains protruding from the surface of the molecule which could contribute to the antibody binding site. To increase the likelihood for correct folding of the mutants the substitutions were selected by comparing the same residues in the different members of the same family. The changes were designed, however, to introduce amino acids with sufficiently dissimilar properties in their side chains (e.g. charge, size, polarity) from the β-hCG residues, to disrupt any Mab binding in this region. Computer graphic model building of the mutant β-hCG molecules ensured that the side chains of the amino acid substitutions could be accommodated into the predicted structure without grossly altering the overall conformation. Table 2 (FIG. 5) summarizes the amino acid changes in eleven of the mutants used in this study.

Expression Vector Construct and Production of Mutants

Full length β-hCG cDNA was cloned from human placental third trimester RNA using RT-PCR and the sense cloning primer 5'ACCGGAATTCCAGGGGCTCCTGCTGTTG3' (SEQ ID NO:1)(corresponding to nucleotide(nt) −51→−33) and the antisense cloning primer 5'TTGGTCGACTTGTGGGAGGATCGGGGTGTCC3' (SEQ ID NO:2)(nt 414→435). The hCG cDNA was cloned into pCDM8[10] into which a DNA fragment from H2-Db containing the 17 membrane proximal amino acid residues, the transmembrane region and cytoplasmic tail had been inserted. This fragment was obtained using RT-PCR amplification using RNA from a spleen of a C57BL/10 mouse with the sense primer 5'GCGTTGGTCGACCATGAGGGGCTGCCTGAGCCC3' (SEQ ID NO:3)(nt 547→566) and an antisense primer 5'CACAGGAGAGACCTGAACACATCG3' (SEQ ID NO:4)(nt 809→832). The sequence of β-hCG is as published[11].

The mutants were produced by an overlap PCR mutagenesis method[12]. Examples of primer sequences that were used include:

mutant 1
sense 5'GAGAACCGCGAGTGCCCCGTGTGCATCACCGTC3' (SEQ ID NO:5);
antisense 5'GGCACTCGCGGTTCTCCACAGCCAGGGTGGC3' (SEQ ID NO:6);
mutant 2
sense 5'CCACTACTGCATCACCGTCAACACCACCATGTGCC3' (SEQ ID NO:7);
antisense 5'CGGTGATGCAGTAGTGGCAGCCCTCCTTCTCC3' (SEQ ID NO:8);
mutant 3
sense 5'GGCTGCCCCTCCCACGTGAACCCCCACGTCTCCTACGCCGTG3' (SEQ ID NO:9);
antisense 5'CGTGGGAGGGGCAGCCAGGGAGCTCGATGGACTCGAAG3' (SEQ ID NO:10);
mutant 4
sense 5'GGAGAACCGCGAGTGCCACTACTGCATCACCGTCAAC3' (SEQ ID NO:11);
antisense 5'GACGGTGATGCACACGTGGCAGCCCTCCTTCTC3' (SEQ ID NO:12);
mutant 5
sense 5'GAGAAGGAGGGCTGCCACGTGTGCATCACCGTC3' (SEQ ID NO:13);
antisense 5'GACGGTGATGCACACGTGGCAGCCCTCCTTCTC3' (SEQ ID NO:14);
mutant 6
sense 5'GAAGGAGGGCTGCCCCTACTGCATCACCGTCAAC3' (SEQ ID NO:15);
antisense 5'GTTGACGGTGATGCAGTAGGGGCAGCCCTCCTTC3' (SEQ ID NO:16).

β-hCG, or the mutants themselves, were used to generate mutants/further mutants.

The sequence of all the mutations were verified using double stranded DNA sequencing (Sequenase USB) and a range of β-hCG internal and CDM8 primers.

Transfections, Surface Expression, Staining and FACs Analysis

COS cells were transfected using a modified DEAE dextran-chloroquine method (based on Seed & Aruffo[13]). Briefly, $1.5 \times 10^6$ cells were seeded into an 80 cm³ flask on the day before transfection. 6 ml of the transfection mixture, (10% NuSerum (Becton Dickinson, Bedford Mass.);1–2 μg/ml supercoiled DNA (CsCl prepared or PEG prepared); 250 μg/ml DEAE dextran) was added to the washed monolayer and left in 37° C. incubator for 60 minutes. Chloroquine was then added to a final concentration of 200 μM and the cells incubated for a further 120 minutes. The transfection mixture was then removed, the monolayer washed with PBS and 3 ml 10%DMSO (in PBS) added for 2 minutes. The cells were washed again and complete medium added. The cells were split 1:1 24 hours later and harvested 65–72 hours after transfection. A transfection efficiency of 20–40% was routinely obtained.

Cells were stained prior to Facs analysis in duplicates of $2 \times 10^5$ cells for each Mab tested. Following washing of the harvested cells with PBS; 10% FCS; 0.02% $NaN_3$. They were incubated with 100 μl of the conformation-dependent anti-β-hCG Mab for 30 minutes on ice, washed twice in PBS 0.02% $NaN_3$ and then incubated with 100 μl of rabbit anti-mouse Fc Flourescein isothyocyanate conjugate. Following washing the cells were fixed in 1% formaldehyde in PBS, and Facs analysis performed using a Becton-Dickinson Facscan. Markers were set on the negative control which was routinely an anti-CD34 IgG1. All cells to the right of this marker were deemed to be positively transfected.

Results

The results of staining wild type and mutant β-hCG expressed on the surface of COS7 cells with the panel of Mabs are summarized in Table 1 . The Mabs to the β1 epitope cluster and the Mab OT3A bind to wild type and all the mutant β-hCG with the same relative binding. This demonstrates that the mutant molecules fold to completely recreate the hCG specific epitope β1. The mutations in the N-terminal hairpin loop (Lys20, Glu21, Gly22, Pro24 and Val25) completely abolish binding of the Mab specific for the β3 and β6 epitope cluster, and lead to partial binding of Mab 3E2 specific for the β3/5 cluster. Different mutants were made to pinpoint the important amino acids that contribute to the binding of the different Mabs.

Mutations of residues Lys20-Glu2-Gly22 (Mutant 1) completely abolish the binding of the Mab InnhCG64 recognizing the hCG-specific epitope cluster β6 and lead to partial binding of the β3/5 Mab 3E2. Mutant 2 (Pro24-Val25) fails to bind both β3 specific Mabs (InnLH1 and InnhCG111) and also reduces binding of 3E2 to 25–50%. The two β3 Mabs have separate but overlapping binding sites on β-hCG, because a single point mutation Pro24→His (Mutant 5) completely abolishes binding of Mab InnLH1 but allows partial binding of InnhCG111 (63%), whereas the mutation Val25→Tyr (Mutant 6) prevents binding of InnhCG111 and reduces the binding of InnLH1 to 63%. Combining all five point mutations of the N-terminal hairpin loop (Mutant 4) is required to reduce the binding of 3E2 to 13% compared to that of OT3A.

In contrast to this the four mutations at residues 68, 74, 75, 79 introduced in the C-terminal hairpin loop (Mutant 3) completely abolish the binding of all cross-reactive antibodies to the mutated molecule yet retain the binding of the hCG-specific Mabs directed to the β1 and β7 epitope clusters and to the linear epitope in the C-terminus of Mab OT3A.

Discussion

The strategy of producing epitope-specific vaccines by allowing the natural folding of a protein to retain a desired discontinuous epitope while at the same time removing unwanted epitopes by mutation, is clearly feasible. It has proved possible to construct mutants which still display epitopes specific for β-hCG, even though they have lost epitopes cross-reacting with luteinizing hormone with which the parent molecule shares 85% homology. Retention of the ability of the mutants to react with the β-hCG-specific monoclonals implies that the structural changes introduced into the molecule have not affected the tertiary folding of the chains which generate the related epitope since this is known to have a discontinuous structure.

The design of the mutants was guided by three main principles. Residues selected for mutation should contribute to epitope formation, they should be common to β-hCG and the cross-reacting luteinizing hormone, and their modification should not significantly influence the overall folding of the molecule at distant sites. The successful deletion mutants clearly achieved the primary objective of preserving the functional structure of the $\beta_1$-specific epitope but considerable progress has also been made towards the secondary aim of identifying the location of the epitopes themselves.

We have shown that, even with a molecule like hCG which has complex non-contiguous B-cell epitopes, it is possible to make radical changes in structure which remove unwanted epitopes yet maintain other desirable epitopes. It seems likely that the many different amino acid substitutions will provide good T-cell helper epitopes. Alternatively, the mutant can either be linked to a carrier such as tetanus toxoid, or engineered as a fusion protein with an appropriately immunogenic partner.

REFERENCES

1. Stevens, V. C., Powell, J. E., Lee, A. C. and Griffin, P. D. Anti-fertility effects from immunization of female baboons with C-terminal peptides of human chorionic gonadotrophin. *Fertil Steril.,* 1981, 36, 98–105.
2. Jones W. R., Judd, S. J., Ing, R. M. Y., Powell, J., Bradley, J., Denholm, E. H., Mueller, U. W., Griffin, P. D., and Stevens, V. C. Phase I clinical trials of a world health organisation birth control vaccine. *Lancet,* Jun. 4, 1988, 1295–1298.
3. Talwar-GP; Singh-O; Pal-R; Chatterjee-N; Sahai-P; Dhall-K; Kaur-J; Das-SK; Suri-S; Buckshee-K; et-al. A vaccine that prevents pregnancy in women. *Proc-Natl-Acad-Sci-U-S-A.* Aug. 30, 1994, 91(18), 8532–6.
4. Hearn, J. B. Immunisation against pregnancy. *Proc R Soc B.,* 1976; 195, 149–60.
5. Dirnhofer, S., Klieber, R., De Leeuw, R., Bidart, J. M., Merz, W. E., Wick, G. and Berger, P. Functional and immunological relevance of the COOH-terminal extension of human chorionic gonadortropin β: implications for the WHO birth control vaccine. *FASEB,* 1993, 7, 1382–1385.
6. Roitt I. M. *Essential Immunology,* 8th Edition. Blackwell Scientific Publications, 1994, p. 281.
7. Roitt, I. M. Basic concepts and new aspects of vaccine development *Parasitology,* 1989, 98 S7–S12.
8. Berger, P., Klieber, R, Panmoung, W., Madersbacher, S., Wolf. H. and Wick, G. Monoclonal antibodes against the free subunits of human chorionic gonadotrophin. *J. Endocrinology,* 1990, 125, 301–309.
9. Dirnhofer, S., Madersbacher, S., Bidart J-M., Ten, P. B. W., Kortenaar Spottie G., Mann, K., Wick, G. and Berger, P. The molecular basis for epitopes on the free β subunit of human chorionic gonadotrophin, its carboxyl terminal peptide and the hCG core fragment *J. of Endocrinology,* 1994, 121,153–162.
10. Seed, B. An LFA-3 cDNA encodes a phospholipid-linked membrane protein homologous to its receptor CD2. *Nature* (Lond.), 1987, 329, 840–842.
11. Talmadge, K, Vamvakopoulos, N. C. and Fiddes, J. C. Evolution of the genes for the beta subunits of human chorionic gonadotropin and luteinizing hormone. *Nature.* 1984, 307, 37–40.
12. Horton, R. M. and Pease, L. R. *Recombination and mutagenesis of DNA sequences using PCR. from Directed Mutagenesis: A Practical Approach,* Ed McPherson, M. J. IRL Press, 1991, 217–247.
13. Seed, B., and Aruffo, A. Molecular cloning of the human CD2 antigen by a rapid immunoselection procedure. *Proc Natl Acad Sci.* USA, 1987, 84, 3365–3369.

What is claimed is:

1. A modified β-hCG protein, the protein amino acid sequence being modified by recombinant means by one or more amino acid substitutions selected from the group consisting of 20 (Lys) to Asn, 21 (Glu) to Arg and 22 (Gly) to Glu; 24 (Pro) to His; 25 (Val) to Tyr; 68 (Arg) to Glu; 74 (Arg) to Ser; 75 (Gly) to His; 79 (Val) to His; and 71 (Gly) to Arg and 74 (Arg) to Ser; so as to reduce the cross-reactivity of the modified β-hCG protein with LH as defined by the ability of both proteins to react with the same antibody, wherein the modified β-hCG protein retains one or more conformational epitopes specific to the native β-hCG.

2. The modified β-hCG protein according to claim 1 being modified by at least amino acid substitution 68 (Arg) to Glu.

3. The modified β-hCG protein according to claim 1 being modified by at least amino acid substitution 74 (Arg) to Ser.

4. The modified β-hCG protein according to claim 1 being modified by at least amino acid substitution 20 (Lys) to Asn, 21 (Glu) to Arg and 22 (Gly) to Glu.

5. The modified β-hCG protein according to claim 1 being modified by at least amino acid substitution 24 (Pro) to His.

6. The modified β-hCG protein according to claim 1 being modified by at least amino acid substitution 25 (Val) to Tyr.

7. The modified β-hCG protein according to claim 1 being modified by at least amino acid substitution 71 (Gly) to Arg, and 74 (Arg) to Ser.

8. The modified β-hCG protein according to claim 1 being modified by at least amino acid substitution 75 (Gly) to His.

9. The modified β-hCG protein according to claim 1 being modified by at least amino acid substitution 79 (Val) to His.

10. The modified β-hCG protein according to claim 1 wherein the protein amino acid sequence is modified by point mutation.

11. The modified β-hCG protein according to claim 1 wherein the modified β-hCG protein is chemically linked by a chemical linkage to an immunogenic substance.

12. The modified β-HCG protein according to claim 11 wherein the chemical linkage is by co-expression as a fusion protein.

13. An isolated and purified nucleic acid sequence encoding a modified β-hCG protein according to claim 1.

14. The isolated and purified nucleic acid according to claim 13 further encoding a fusion protein comprising an immunogenic carrier protein fused to the modified β-hCG protein.

15. An expression vector comprising a nucleic acid according to claim 13.

16. An expression vector comprising a nucleic acid according to claim 14.

17. A mammalian host cell comprising a vector according to claim 15.

18. A mammalian host cell comprising a vector according to claim 16.

19. A mammalian host cell comprising nucleic acid according to claim 13.

20. A mammalian host cell comprising nucleic acid according to claim 14.

21. A microbial host cell comprising a vector according to claim 15.

22. A microbial host cell comprising a vector according to claim 16.

23. A microbial host cell comprising nucleic acid according to claim 13.

24. A microbial host cell comprising nucleic acid according to claim 14.

25. A composition comprising a modified β-hCG protein according to claim 1 and a pharmaceutically acceptable carrier.

26. A composition comprising a nucleic acid according to claim 13 and a pharmaceutically acceptable carrier.

27. A composition comprising a nucleic acid according to claim 14 and a pharmaceutically acceptable carrier.

28. A composition comprising an expression vector according to claim 15 and a pharmaceutically acceptable carrier.

29. A composition comprising an expression vector according to claim 16 and a pharmaceutically acceptable carrier.

30. A contragestative composition, comprising a modified β-hCG protein according to claim 1 and a pharmaceutically acceptable carrier.

31. A modified β-hCG protein having a contragestative function in a female mammal, wherein the modified β-hCG protein has an amino acid sequence that is modified by recombinant means by one or more amino acid substitutions selected from the group consisting of 20 (Lys) to Asn, 21 (Glu) to Arg and 22 (Gly) to Glu; 24 (Pro) to His; 25 (Val) to Tyr; 68 (Arg) to Glu; 74 (Arg) to Ser; 75 (Gly) to His; 79 (Val) to His; and 71 (Gly) to Arg and 74 (Arg) to Ser; so as to reduce the cross-reactivity of the modified β-hCG protein with LH as defined by the ability of both proteins to react with the same antibody, wherein the modified β-hCG protein retains one or more conformational epitopes specific to the native β-hCG.

32. A modified β-hCG protein according to claim 31 being modified by at least an amino acid substitution 68 (Arg) to Glu.

33. A modified β-hCG protein according to claim 31 being modified by at least an amino acid substitution 74 (Arg) to Ser.

\* \* \* \* \*

SEQUENCE LISTING

```
<160> NUMBER OF SEQ ID NOS: 16

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:  Beta-hcG
      Human Sense Cloning Primer

<400> SEQUENCE: 1
accggaattc caggggctcc tgctgttg                                        28

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:  Beta-hcG
      Human Antisense Cloning Primer
```

```
<400> SEQUENCE: 2
ttggtcgact tgtgggagga tcggggtgtc c                              31

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: C57BL/10
      Mouse Sense Primer

<400> SEQUENCE: 3
gcgttggtcg accatgaggg gctgcctgag ccc                            33

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: C57BL/10
      Mouse Antisense Primer

<400> SEQUENCE: 4
cacaggagag acctgaacac atcg                                      24

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Mutant 1
      Sense Primer

<400> SEQUENCE: 5
gagaaccgcg agtgccccgt gtgcatcacc gtc                            33

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Mutant 1
      Antisense Primer

<400> SEQUENCE: 6
ggcactcgcg gttctccaca gccagggtgg c                              31

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Mutant 2
      Sense Primer

<400> SEQUENCE: 7
ccactactgc atcaccgtca acaccaccat gtgcc                          35

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Mutant 2
      Antisense Primer
```

```
<400> SEQUENCE: 8
cggtgatgca gtagtggcag ccctccttct cc                                    32

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence:  Mutant 3
      Sense Primer

<400> SEQUENCE: 9
ggctgcccct cccacgtgaa cccccacgtc tcctacgccg tg                         42

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:  Mutant 3
      Antisense Primer

<400> SEQUENCE: 10
cgtgggaggg gcagccaggg agctcgatgg actcgaag                              38

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:  Mutant 4
      Sense Primer

<400> SEQUENCE: 11
ggagaaccgc gagtgccact actgcatcac cgtcaac                               37

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:  Mutant 4
      Antisense Primer

<400> SEQUENCE: 12
gacggtgatg cacacgtggc agccctcctt ctc                                   33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence:  Mutant 5
      Sense Primer

<400> SEQUENCE: 13
gagaaggagg gctgccacgt gtgcatcacc gtc                                   33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:  Mutant 5
      Antisense Primer

<400> SEQUENCE: 14
```

-continued

```
gacggtgatg cacacgtggc agccctcctt ctc                                33
```

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Mutant 6
      Sense Primer

<400> SEQUENCE: 15

```
gaaggagggc tgcccctact gcatcaccgt caac                               34
```

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Mutant 6
      Antisense Primer

<400> SEQUENCE: 16

```
gttgacggtg atgcagtagg ggcagccctc cttc                               34
```